(12) United States Patent
Lee

(10) Patent No.: US 7,601,884 B2
(45) Date of Patent: Oct. 13, 2009

(54) METHOD OF PRODUCING CLONED ANIMALS BY DEMECOLCINE TREATMENT

(75) Inventor: Eunsong Lee, Seoul (KR)

(73) Assignee: KNU - Industry Cooperation Foundation, Gangwon-do (KR)

( * ) Notice: Subject to any disclaimer, the term of this patent is extended or adjusted under 35 U.S.C. 154(b) by 0 days.

(21) Appl. No.: 11/968,745

(22) Filed: Jan. 3, 2008

(65) Prior Publication Data

US 2008/0301828 A1    Dec. 4, 2008

(30) Foreign Application Priority Data

May 29, 2007    (KR) .................... 10-2007-0052034

(51) Int. Cl.
C12N 15/00    (2006.01)
C12N 5/00    (2006.01)
C12N 5/02    (2006.01)
A01K 67/027    (2006.01)

(52) U.S. Cl. .................. 800/24; 800/14; 435/375; 435/377

(58) Field of Classification Search .......... 800/24, 800/14; 435/375, 377
See application file for complete search history.

(56) References Cited

U.S. PATENT DOCUMENTS

| | | | |
|---|---|---|---|
| 4,994,384 A | 2/1991 | Prather et al. | |
| 5,057,420 A | 10/1991 | Massey | |
| 5,945,577 A | 8/1999 | Stice et al. | |

FOREIGN PATENT DOCUMENTS

| | | | |
|---|---|---|---|
| EP | 0 930 009 A1 | 7/1999 | |
| KR | 2001-0005423 A | 1/2001 | |
| WO | 99/01164 A1 | 1/1999 | |
| WO | 99/34669 A1 | 7/1999 | |
| WO | 99/37143 A2 | 7/1999 | |

OTHER PUBLICATIONS

Vogel, N, 2003,Science, 300:225-227.*
Simerly et al. , 2003, Science, 300:297.*
Mitalipov, 2006, Methods in Mol. Bio, 348: 151-168.*
Baguisi and Overstrom, 2000, Theriogenology 53:209.*
Gasparrini et al, 2003, Biology of Reproduction, 68:1259-1266.*
Galli et al, 2002, Cloning and Stem Cells, 4:189-196.*
Kawakami et al, 2003, Cloning and Stem Cells, 5:379-387.*
Russell et al, 2005, Molecular Reproduction and Development, 72:161-170.*
Ibanez et al, 2003, Biology of Reproduction, 68:1249-1258.*
M Kanda, et al; "Early embryonic development in vitro and embryo transfer in the cat", (Abstract Only) J. Vet. Med. Sci., 57(4): 641-646, 1995.
H. Nagashima, et al; "Nuclear transfer of porcine embryos using cryopreserved delipated blastomeres as donor nuclei" (Abstract Only), Mol. Reprod. Dev. 48:339-343 1997.
RS Prather, et al; "Nuclear transplantation in early pig embryos", (Abstract Only), Biol. Reprod. 41:414-418, 1989.
BD Bavister, et al; "Development of preimplantation embryos of the golden hampster in a defines culture medium", (Abstract Only) Biol. Repord 28, 235-240, 1983.
Yoonee Park, et al; "Effect of exogenous carbohydrates in serum-free culture medium on the development of in vitro matured and fertilized porcine embryos" (Abstract Only), Zygote 2005, 13,269-270, 2005.
S.M. Willadsen; "Nuclear transplantation in sheep embryos", Nature, 320:63-65, 1986.
R.S. Prather, et al; "Nuclear Transplantation in the Pig Embryo: Nuclear Swelling", J. Exp. Zool. 255: 355-358, 1990.
S.L.Terlouw, et al; "In Vitro Development of Nuclear Transplant Pig Embryos", Theriogenology 37: 309, 1992.
Shawn C. Walker, et al; "A Highly Efficient Method for Porcine Cloning by Nuclear Transfer Using In Vitro-Matured Oocytes", Cloning Stem Cells, 4, 105-110, 2002.

* cited by examiner

Primary Examiner—Valarie Bertoglio
(74) Attorney, Agent, or Firm—Ladas & Parry LLP

(57) ABSTRACT

A cloned animal is produced by demecolcine treatment characterized by culturing the nuclear transfer embryo in vitro and transferring the embryo in vivo. This significantly improves in vitro development of somatic cell nuclear transfer embryos and maintenance of pregnancy from transfer of transfer somatic cell nuclear transfer embryos in a surrogate mother up to delivery. A nuclear transfer embryo of a non-primate mammal made by enucleating a recipient oocyte; injecting a nuclear donor cell into the enucleated oocyte; fusing together the injected enucleated oocyte with the injected nuclear donor cell to form a fused oocyte; activating the fused oocyte; and treating the activated oocyte with demecolcine to form the nuclear transfer embryo.

18 Claims, No Drawings

METHOD OF PRODUCING CLONED ANIMALS BY DEMECOLCINE TREATMENT

BACKGROUND OF THE INVENTION

1. Field of the Invention

The present invention relates to a method of producing a cloned animal by demecolcine treatment. More particularly, the present invention relates to a method of effectively producing a cloned animal by producing a nuclear transfer embryo of an animal treated with demecolcine after activation of a fused oocyte, culturing the nuclear transfer embryo in vitro, and transferring the nuclear transfer embryo in vivo.

2. Description of the Related Art

With the recent development of somatic cell nuclear transfer (SCNT) technology by cell fusion or intracytoplasmic cell injection, animals are actually being cloned. SCNT technology, which allows living offspring to be born without undergoing meiosis and haploid germ cell retention which generally occur in a generative process, is a method of developing new individuals by transferring diploid somatic cells of adults into enucleated cells to create embryos and then transferring the embryos in vivo.

Such SCNT technology can be widely used in the field, for example, in the propagation of superior animals, conservation of rare or nearly extinct animals, production of certain nutrients, production of therapeutic bio-materials, production of animals for organ transplantation, production of animals with diseases or disorders, and production of animals medically suitable for alternative treatments to organ transplantation such as gene therapy.

Animal cloning was first accomplished by Dr. Wilmut of the Roslin Institute, England, by taking a mammary gland cell from a six-year old female sheep, transferring the cell into an enucleated oocyte to prepare a nuclear transfer embryo, and transferring the embryo in vivo, thereby producing a cloned sheep named Dolly. Thereafter, it was reported that cloned cows, mice, goats, pigs and rabbits were produced by nuclear transfer using somatic cells (see WO 9937143A2, EP 930009A1, WO 9934669A1, WO 9901164A1 and U.S. Pat. No. 5,945,577).

However, it is very difficult to implement cloning by any of these methods due to low in vitro and in vivo development rates of the SCNT embryos. Particularly, pigs showed very low in vitro development to blastocyst, had low number of cells, and showed discontinuous development of fertilized embryos cloned since in vivo transfer. Thus, to efficiently produce a cloned pig, a novel method was needed to improve the development to blastocyst, a stage prior to the implantation of NT embryos.

Accordingly, while researching an improved method of producing a cloned animal using SCNT technology, the present inventors found that in vitro development of a nuclear transfer embryo was significantly improved by treatment with a specific chemical, demecolcine, after the fused nuclear transfer embryo was activated during the process of producing a cloned animal using SCNT technology. Also, maintenance of pregnancy from transfer of the embryos in a surrogate mother to delivery significantly improved compared to the control group. These experimental findings are the basis of the present invention.

SUMMARY OF THE INVENTION

The invention is therefore directed to providing a method of producing a nuclear transfer embryo of an animal using somatic cell nuclear transfer technology, characterized in that a fused nuclear transfer embryo is activated and treated with demecolcine (DEM).

The invention is also directed to providing a method of producing a cloned animal, characterized in that the fused nuclear transfer embryo is activated and treated with DEM, and then cultured in vitro and transferred in vivo.

[Definitions of Terms]

The term 'nuclear transfer' as used herein refers to a gene manipulation technique that yields identical characteristics and qualities by artificially combining an enucleated cell with nuclear DNA of one cell.

The term "nuclear transfer embryo" as used herein refers to an embryo injected or fused with a nuclear donor cell.

The term "cloned" as used herein refers to a gene manipulation technique for preparing a new individual unit to have a gene set identical to another individual unit. In particular, the term "cloned" is used herein to mean that a cell, an embryonic cell, a fetal cell, and/or an animal cell has a nuclear DNA sequence substantially similar or identical to the nuclear DNA sequence of another cell.

The term "nuclear donor cell" as used herein refers to a cell or a nucleus from a cell which transfers the nucleus into a recipient oocyte functioning as a nuclear acceptor.

The term "recipient oocyte" as used herein refers to an oocyte which receives a nucleus from a nuclear donor cell after an original nucleus has been removed through enucleation.

The term "mature oocyte" as used herein refers to an oocyte which has preferably reached the metaphase ∥ of meiosis.

The term "enucleated oocyte" as used herein refers to an oocyte which its nucleus has been removed.

The term "fusion" as used herein refers to a combination between a nuclear donor and a lipid membrane of a recipient oocyte. For example, the lipid membrane may be the plasma membrane or nuclear membrane of a cell. Fusion may occur upon application of an electrical stimulus between a nuclear donor and a recipient oocyte when they are placed adjacent to each other or when a nuclear donor is placed in a perivitelline space of a recipient oocyte.

The term "activation" as used herein refers to stimulation of a cell to divide, before, during or after nuclear transfer. Preferably, in the present invention, it means stimulation of a cell to divide after nuclear transfer.

The term "live offspring" as used herein refers to an animal which can survive ex utero. Preferably, it is an animal which can survive for one second, one minute, one day, one week, one month, six months, or more than one year. The animal may not require an in utero environment for survival.

The present invention is characterized in that a fused nuclear transfer embryo is treated with DEM after its activation when a cloned animal is produced using somatic cell nuclear transfer (SCNT) technology, thereby significantly improving in vitro development of the nuclear transfer embryo, and enhancing maintenance of pregnancy from transfer to delivery.

In one aspect, the present invention provides a method of producing a nuclear transfer (NT) embryo of an animal which includes enucleating a recipient oocyte, injecting a nuclear donor cell, fusing the injected nuclear donor cell with the enucleated recipient oocyte, and activating the fused oocyte, including: treating the activated oocyte with DEM.

Herein, the animal may include mammals such as sheep, cows, mice, goats, pigs and rabbits, but preferably pigs.

Step 1: Enucleation of Recipient Oocytes

The recipient oocytes may employ immature oocytes taken from an ovary of an animal to be cloned, which are induced to in vitro maturation. Preferably, the immature oocytes of the animal are cultured in a medium for in vitro maturation, and therefrom only mature oocytes having first polar bodies extruded are collected.

The culture media for in vitro maturation of the immature oocytes are well known in the art, and TCM199 [containing 5 IU eCG (equine chorionic gonadotrophin), 5 IU hCG (human chorionic gonadotrophin), 10 ng/ml surface growth factor, 1 µg/ml insulin, and 0.6 mM cysteine] is used herein.

After the uptake of the mature oocytes, haploid nuclei are removed from the oocytes. The enucleation of the oocytes may be performed using any method well-known in the art (see U.S. Pat. No. 4,994,384; U.S. Pat. No. 5,057,420; U.S. Pat. No. 5,945,577; EP Patent No. 0930009 A1; Korean Patent No. 342437; Kanda et al., *J. Vet. Med. Sci.,* 57(4):641-646, 1995; Willadsen, *Nature,* 320:63-65, 1986, Nagashima et al., *Mol. Reprod. Dev.* 48:339-343 1997; Nagashima et al., *J. Reprod. Dev.* 38:37-78, 1992; Prather et al., *Biol. Reprod.* 41:414-418, 1989, Prather et al., *J. Exp. Zool.* 255:355-358, 1990; Saito et al., *Assis Reprod Tech Andro,* 259:257-266, 1992; Terlouw et al., *Theriogenology* 37:309, 1992).

Preferably, the enucleation of recipient oocytes can be performed by either of the following two methods. One method includes removing a cumulus cell of a mature recipient oocyte, partially dissecting the zona pellucida of the recipient oocyte using a needle by making a slit near the first polar body, and removing the first polar body, nucleus and cytoplasm (in the smallest amount possible) through the slit. The other method includes removing a cumulus cell of a mature recipient oocyte, staining the oocyte, and removing the first polar body and nucleus of the oocyte using an aspiration pipette. Preferably, for the enucleation of oocytes, the aspiration method is used for oocytes with high viability, whereas, the method of forming a slit is used for oocytes with low viability, decided by visual examination of the recipient oocytes.

Step 2: Infection of Nuclear Donor Cells

Somatic cells derived from target animals to be cloned can be used as nuclear donor cells. Particularly, somatic cells used herein may originate from tissue such as the cumulus, skin, oral mucosa, blood, bone marrow, liver, lungs, kidneys, muscles, reproductive organs, etc. that are yielded from embryonic cells, fetal cells, juvenile cells, or preferably adult cells. Examples of somatic cells which can be used herein may include, but are not limited to, cumulus cells, epithelial cells, fetal fibroblasts, nervous cells, keratinocytes, hematopoietic cells, melanocytes, chondrocytes, erythrocytes, macropharges, monocytes, muscle cells, B lymphocytes, T lymphocytes, embryonic stem cells, embryonic reproductive cells, fetal cells, placenta cells, and embryonic germ cells. More preferably, the somatic cells used herein may be fetal fibroblasts.

In the embodiment, fetal fibroblasts taken from ear tissue of a newborn pig are used (see Experimental Example 2). If the target animals to be cloned are swine, these may include but are not limited to swine of Landrace and Yorkshire species. And, depending on the purpose, miniature swine may be used.

Furthermore, the nuclear donor cells used herein may be obtained by transforming wild-type somatic cells with specific genes using a gene transfer method or a gene targeting method. Both the gene transfer method and gene targeting method are well known in the art.

Somatic cells which are provided as the nuclear donor cells can be obtained by a method of preparing surgical samples or biopsy samples. Single cells can be obtained from samples using any method well known in the art. For example, tissue from an animal to be cloned is aseptically dissected to obtain a surgical sample or a biopsy sample. Then, the sample is chopped, treated with trypsin and then cultured in tissue culture medium. After culturing in the medium for 3-4 days and confirming full growth of cells on a culture dish, some of the tissue is frozen and stored in liquid nitrogen for later use, and the remnants are subcultured for use in nuclear transfer. The cells to be continuously cultured for use in nuclear transfer are subcultured up to 15 times to prevent excessive growth.

The tissue culture medium may be any that is well known in the art, for example, TCM-199 or DMEM (Dulbecco's Modified Eagle's Medium).

In the embodiment, fetal fibroblasts taken from the ear tissue of a newborn pig are cultured for 5-7 days in DMEM/F12 medium containing 10% bovine fetal serum until a monolayer is formed, and treated with trypsin on the day of nucleus transfer to prepare cell suspension for use in nuclear transfer.

The transfer of nuclear donor cells is performed by microinjecting them into a perivitelline space of the enucleated oocytes using a micropipette.

Step 3: Fusion

The enucleated oocytes previously injected with the nuclear donor cells are electrically fused with the nuclear donor cells by using a cell manipulator. Electric current used herein may be either alternating current (AC) or direct current (DC), and herein direct current is applied twice each at 1.4 to 1.8 kV/cm for 20 to 40 µsec to induce fusion of the oocytes with the nuclear donor cells.

Step 4: Activation of Nuclear Transfer Embryos

Activation of fused NT embryos is a step of reactivating a temporarily arrested cell-cycle. To this end, it is necessary to reduce the activity of cell signal delivery materials such as MPF, MAP kinase etc., which are factors of cell cycle arrest. Generally, methods of activating NT embryos include an electrical method and a chemical method. In the present invention, it is preferable to activate the NT embryos by the electrical method.

That is, in the embodiment, after being neutralized in an activation medium for 3 minutes, the fused NT embryos are transferred to a fresh activation medium (cell interval: 1 mm) in an electrode chamber and led to activation by applying direct voltage twice at 1.2 kV/cm for 60 µsec. The embryo activation medium used herein is 0.28M mannitol solution containing 0.01 mM $CaCl_2$ and 0.05 mM $MgCl_2$ (Walker et al., *Cloning Stem Cells,* 4, 105-11, 2002).

Step 5: Demecolcine Treatment

After being stimulated for activation, the fused embryos are treated with DEM. It is preferable that the treatment be performed under appropriate conditions to trigger changes in cell cycle and morphology of chromosomal DNA by reaction of the nucleus of the cell. More preferably, DEM is treated at a concentration of 0.02 to 1.0 µg/ml for 2 to 12 hours.

In an experimental example of the present invention, it can be noted that in vitro development to blastocysts of NT porcine embryos previously treated with DEM (see Experimental Example 1) has significantly improved compared to a comparative example (see Table 1).

Further, in another experimental example of the present invention, it can be noted that in vitro development to blastocysts of NT porcine embryos previously treated with DEM (see Experimental Example 4) is slightly dependant on the time of DEM treatment, but exhibits the highest level of growth during a 4-hour incubation period (see Table 1).

In another aspect, the present invention provides a method of producing cloned animals, which includes enucleating recipient oocytes, injecting nuclear donor cells, fusing the injected nuclear donor cells with the enucleated recipient oocytes, activating the fused nuclear transfer embryos, and culturing a somatic cell nuclear transfer embryos in vitro and transferring the embryos in vivo, including the step of treating the activated oocyte with DEM.

In vitro culture of somatic cell NT embryos may be performed in in vitro culture medium that is well known in the art for 30 minutes to 7 days depending on the purpose of use, such as in vitro development and embryo transfer. In vivo transfer may be performed on estrous target animals to be cloned as surrogate mothers. In one embodiment of the present invention, estrous gilt is the recipient animal. Particularly, under inhalation anesthesia, the abdomen of the pig is cut open, thereby exposing ovaries and oviducts, and somatic cell NT embryos are transferred into the oviduct.

In one experimental example of the present invention, it can be seen that delivery rate and the number of a pigs born alive in a litter of the recipient pig treated with DEM (see Experimental Example 3) are significantly higher compared to the comparative example not treated with DEM (see Table 3).

Hereinafter, the particular methods of the present invention will be described in detail with reference to exemplary embodiments, but the scope of the present invention will not be limited thereto.

DETAILED DESCRIPTION OF THE INVENTION

The present invention will now be described more fully hereinafter with reference to the accompanying drawings, in which exemplary embodiments of the invention are shown.

Exemplary Embodiment 1

Preparation of Recipient Oocytes

Follicle contents were aspirated from 3-8 mm diameter follicle present on a surface of a pig ovary obtained from a butcher. Among them, only oocytes surrounded with a multi-layered cumulus cell and having uniform cell mass were selected to be used for in vitro maturation. In vitro maturation medium for immature pig oocytes used herein was TCM-199 [containing 5 IU equine chorionic gonadotrophin (eCG), 5 IU human chorionic gonadotrophin (hCG), 10 ng/ml of surface growth factor, 1 µg/ml of insulin, and 0.6 mM of cysteine]. The immature oocytes were cultured in the in vitro maturation culture medium at 39° C., under an atmosphere of 5% $CO_2$ for 22 hours, and further cultured in fresh culture medium without eCG and hCG for 16 to 20 hours to promote maturation of the oocytes.

Exemplary Embodiment 2

Preparation of Nuclear Donor Cells

Fetal fibroblasts taken from ear tissue of a newborn pig were cultured in DMEM/F12 medium containing 10% bovine fetal serum for 5 to 7 days until a monolayer was formed. The resulting cells were treated with trypsin on the day of nuclear transfer to prepare a cell suspension which was used for nuclear transfer.

Exemplary Embodiment 3

Production of Somatic Cell Nuclear Transfer (NT)
<3-1> Enucleation of Recipient Oocytes After 38 to 42 hours of in vitro maturation of the oocytes according to Exemplary Embodiment 1, the matured oocytes were transferred to an in vitro maturation culture medium containing 0.1% (w/v) hyaluronidase, and then the cumulus cells attached to the oocytes were gently aspirated using a pipette. After the removal of the cumulus cells, morphologically normal oocytes were selected and washed twice with TLH-BSA for use in nuclear transfer. The oocytes matured in vitro were incubated in micro-manipulation culture medium containing 5 µg/ml cytochalasin B and 5 µg/ml bis-benzimide for 10 to 15 minutes and then transferred to a drop of the micro-manipulation culture medium to remove a first polar body and metaphase chromosome using an enucleation pipette (inner diameter: 16-17 mm) by aspiration. In this step, the oocytes were momentarily exposed to UV radiation to confirm enucleation. The enucleated oocytes were incubated in fresh micro-manipulation medium at 39° C. until the micro-injection of nucleus donor cells. The medium for micro-manipulation of the oocytes used herein was HEPES buffered Tyrode's medium (Bavister et al., *Biol Reprod* 28, 235-24, 1983) containing 0.4% (w/v) bovine serum albumin and 0.6 mM cysteine. The in vitro culture medium for NT embryos was North Carolina State University-23 (NCSU-23) culture medium without glucose and containing 0.5 mM pyruvate and 0.5 mM lactate (Park et al., *Zygote* 2005, 13, 269-27, 2005).

<3-2> Injection of Nuclear Donor Cells

Drops for oocytes and nuclear donor somatic cells were placed on a micro-manipulation dish. 15 to 20 somatic cells were aspirated using a cell injection pipette (inner diameter: 16-17 mm), and then each cell was injected into a perivitelline space of each oocyte.

<3-3> Electrical Cell Fusion

In Exemplary Embodiment <3-2>, somatic cell nuclear transfer (SCNT) embryos produced by injection of the nuclear donor cells were incubated in fusion medium for 3 minutes, and interposed between two electrodes spaced 1 mm apart from each other in the fusion medium. The fusion of the oocytes with the nuclear donor cells was induced by direct voltage applied twice at 1.4 to 1.8 kV/cm for 20 to 40 µsec. After electrical stimulation, the NT embryos were washed in micro-manipulation culture medium three times and incubated in in vitro culture medium for 1 hour until activation treatment. The cell fusion culture medium used was 0.28M mannitol solution containing 0.001 mM $CaCl_2$ and 0.05 mM $MgCl_2$. All oocytes were manipulated (including micro-manipulation) at 39° C.

<3-4> Activation of Embryos

After being neutralized in an activation medium for 3 minutes, the fused NT embryos were transferred to an electrode chamber (interval: 1 mm) containing activation medium, and stimulated by direct voltage applied twice at 1.2 kV/cm for 60 µsec. The activation medium used was 0.28M mannitol solution containing 0.01 mM $CaCl_2$ and 0.05 mM $MgCl_2$ (Walker et al., *Cloning Stem Cells*, 4, 105-11, 2002).

<3-5> Demecolcine Treatment

After the activation stimulation, the activated embryos were incubated in NCSU-23 culture medium containing 0.4 µg/ml demecolcine (DEM) (Sigma-Aldrich Corp., USA) for 4 hours.

Comparative Example 1

With the same method as in Exemplary Embodiment <3-4>, the fused NT embryos were electrically activated, but not treated with DEM.

Exemplary Embodiment 4

In Vitro Culture and In Vivo Transfer of SCNT Embryos

After activation stimulation, the SCNT embryos were cultured in in vitro culture medium for 6 days in an atmosphere of 5% $CO_2$, 5% $O_2$ and 90% $N_2$ gas.

For in vivo transfer of the NT embryos, a naturally-estrous gilt was used as a recipient animal. On the day of the production of the NT embryos, a standing estrus pig was subjected to inhalation anesthesia, and using a common method, cut open to expose the ovaries and oviducts. After confirming the presence of follicle, ovulation and corpus luteum in the ovary, 90 to 160 SCNT embryos activated and treated with DEM were transferred into the oviduct by fimbriae. The recipient pig into which the NT embryos were transferred was monitored to confirm whether or not it was estrus, and a pregnancy test was taken every two weeks, 4 weeks after transfer of the fertilized embryos. When the recipient pig gave birth to live, SCNT embryo-derived offspring, its period of pregnancy, the number of live offspring, their weight, and morphological abnormalities found in any of the live offspring were monitored and recorded.

Experimental Example 1

Improvement of In vitro Development of SCNT Porcine Embryos by DEM Treatment

The SCNT embryos of Exemplary Embodiment 3 and Comparative Example 1 were cultured in vitro with an atmosphere of 5% $CO_2$, 5% $O_2$ and 90% $N_2$ gases. On the second and sixth days of the in vitro culture, their division rates and development to blastocysts were monitored. Further, the blastocysts were stained with bis-benzimide to estimate the number of cells under a fluorescent microscope.

As a result, it can be seen that development to blastocysts of the embryos treated with DEM, followed by being cultured in vitro, significantly improved over Comparative Example 1 which was not treated with DEM (see Table 1).

TABLE 1

Development to Blastocysts of SCNT Embryos

| Group | N | ≧2-Cell(%) | Blastocyst(%) | No. of Cells/Blastocysts |
|---|---|---|---|---|
| Comparative Example 1 (w/o DEM) | 188 | 146(77.7) | 30(16.0) | 38.8 |
| Exemplary Embodiment 3 (w/ DEM) | 187 | 144(76.8) | 51(27.3) | 39.5 |

Experimental Example 2

Effect of DEM Treatment on Production of Pseudo-Pronuclei of SCNT Embryos

The oocytes treated with DEM of Exemplary Embodiment 3 or the oocytes of Comparative Example 1 were cultured in vitro for 7 hours, activated, fixed for 11 hours, and stained to estimate the number of pseudo-pronuclei and their production rate. The fixation of the oocytes was performed using a whole-mount method. 10 to 20 oocytes were placed on a slide glass and covered with a cover glass. The oocytes were fixed in a fixative (25% acetic acid in ethanol) at 33° C. for 10 to 20 minutes. The fixed oocytes were stained with 1% orcein (in 45% acetic acid solution) and then the pseudo pronuclei were observed by a phase microscope.

The results show that one pseudo pronucleus was produced from a single SCNT embryo treated with DEM (see Table 2). This means that DEM brings about a morphological change of the nuclear donor cell introduced to the oocyte, and hence effectively maintains chromosomal DNA in a polyploidy (2n) state.

TABLE 2

Production of Pseudo Pronuclei from SCNT Embryos

| Group | N | 1PPN**(%) | Multi-PPN***(%) | Others(%) |
|---|---|---|---|---|
| Comparative Example 1 (w/o DEM) | 42 | 26(61.9) | 13(31.0) | 3(7.1) |
| Exemplary Embodiment 3 (w/ DEM) | 43 | 36(83.7) | 4(9.3) | 3(7.0) |

**1PPN: one pseudo pronucleus
***Multi-PPN: 2 or more pseudo pronuclei

Experimental Example 3

Effect of DEM Treatment on Delivery Rate and Number of Pigs Born Alive

The effect of DEM treatment to the SCNT embryos on delivery rate and the number of pigs born alive was surveyed. Each group of SCNT embryos (107-160/a recipient pig), wherein one was treated with DEM according to Exemplary Embodiment 4 and the other (102-165/a recipient pig) was not treated with DEM, was transferred into 8 to 10 recipient pigs monitored to see whether or not they were estrus. Starting 4 weeks after transfer of the fertilized embryos, they were given pregnancy tests every 2 weeks. When they gave birth to live, SCNT embryo-derived offspring, the period of pregnancy, the number of live offspring, their weight and any morphological abnormalities were monitored and recorded. Further, the number of recipient pigs having live offspring and the number of pigs born alive in a litter were surveyed.

As a result, the delivery rate and number of pigs born alive in a litter of the recipient pig transferred with SCNT embryos treated with DEM significantly increased compared to Comparative Example 1, in which there was no treatment with DEM (see Table 3).

TABLE 3

Delivery Rate and Number of Pigs Born Alive

| Group | N | No. of Recipient Pigs Delivered(%) | No. of Pigs Born Alive(%) | No. of Pigs/Litter |
|---|---|---|---|---|
| Comparative Example 1 (w/o DEM) | 10 | 3(30.0) | 7 | 2.3 |
| Exemplary Embodiment 3 (w/ DEM) | 8 | 4(50.0) | 12 | 3.0 |

Experimental Example 4

In Vitro Development Rate of SCNT Embryos According to Time of DEM Treatment

Change in in vitro development of SCNT embryos depending on the time of DEM treatment was surveyed. The SCNT embryos activated according to Exemplary Embodiment <3-4> were incubated in NCSU-23 culture medium containing 0.4 μg/ml DEM for 2, 4 and 6 hours, respectively, and cultured in vitro by the same method as described in Experimental Example 1, followed by observation of their development to blastocysts.

The results show that there wasn't a significant change in in vitro development of the SCNT embryos according to the time of DEM treatment. However, they exhibited the highest level of growth during a 4-hour incubation period (see Table 4).

TABLE 4

Development of SCNT Embryos according to Time of DEM Treatment

| Group | N | ≧2 cells (%) | Blastocysts (%) | No. of Cells/Blastocysts |
|---|---|---|---|---|
| DEM-treated Group (2 hrs) | 141 | 119(84.4) | 35(24.8) | 35.3 ± 2.1 |
| DEM-treated Group (4 hrs) | 142 | 114(80.3) | 42(29.6) | 35.2 ± 1.8 |
| DEM-treated Group (6 hrs) | 142 | 111(78.2) | 36(25.4) | 30.8 ± 2.7 |

The present invention significantly improves in vitro development of SCNT embryos. Also, the present invention enhances maintenance of pregnancy from transfer of SCNT embryos into a surrogate mother up to delivery.

While the invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of producing a nuclear transfer embryo of a non-primate mammal comprising the steps of:
    enucleating a recipient oocyte isolated from a non-primate mammal;
    injecting a nuclear donor cell of the same species as the oocyte into the enucleated oocyte;
    fusing together the injected enucleated oocyte with the injected nuclear donor cell to form a fused oocyte;
    activating the fused oocyte; and
    treating the activated oocyte with demecolcine followed by removal of the demecolcine to form the nuclear transfer embryo.

2. The method according to claim 1, wherein the demecolcine treatment of the activated oocyte is carried out at a demecolcine concentration of 0.02 to 1.0 μg/ml for a duration of 2 to 12 hours.

3. The method according to claim 1, wherein the non-primate mammal is selected from the group consisting of a sheep, a cow, a mouse, a goat, a pig and a rabbit.

4. The method according to claim 3, wherein the non-primate mammal is a pig.

5. A method of producing a cloned non-primate mammal comprising the steps of:
    enucleating a recipient oocyte isolated from a non-primate mammal;
    injecting a nuclear donor cell of the same species as the oocyte into the enucleated oocyte;
    fusing the enucleated oocyte and the injected nuclear donor cell to form a fused oocyte;
    activating the fused oocyte;
    treating the activated oocyte with demecolcine followed by removal of the demecolcine to form a somatic cell nuclear transfer (SCNT) embryo;
    culturing in vitro the SCNT embryo; and
    transferring in vivo the SCNT embryo into a surrogate mother of the same species as the embryo wherein the surrogate mother gives birth to produce a non-primate mammalian clone.

6. The method according to claim 5, wherein the demecolcine treatment is carried out at a demecolcine concentration of 0.02 to 1.0 μg/ml for a duration of 2 to 12 hours.

7. The method according to claim 5, wherein the non-primate mammal is selected from the group consisting of a sheep, a cow, a mouse, a goat, a pig and a rabbit.

8. The method according to claim 5, wherein the non-primate mammal is a pig.

9. The method according to claim 5 wherein the step of fusing comprises subjecting the enucleated oocyte containing the injected nuclear donor cell to a voltage applied twice at 1.4 kV/cm for 20 to 40 μsec, such that the electrical field is either a direct current electrical field or an alternating current electrical field.

10. The method according to claim 5 wherein the step of fusing comprises providing a cell fusion culture medium comprising 0.28 M mannitol, 0.001 mM $CaCl_2$, and 0.05 mM $MgCl_2$.

11. The method according to claim 5 wherein the demecolcine treatment comprises incubating the activated oocyte with an atmosphere comprising 5% $CO_2$, 5% $O_2$ and 90% $N_2$.

12. The method according to claim 5 wherein the step of activating comprises transferring the fused oocyte into a fresh activation medium comprising a 0.28 M mannitol solution comprising, 0.001 mM $CaCl_2$, and 0.05 mM $MgCl_2$ and subjecting the fused oocyte to direct voltage applied twice at 1.2 kV/cm for 60 μsec.

13. The method according to claim 5 wherein the oocyte, prior to enucleation, is cultured in a maturation medium containing 5 IU of equine chorionic gonadotropin (eCG), 5 IU of human chorionic gonadotropin (hCG), 10 ng/ml of surface growth factor, 1 μg/ml of insulin and about 0.6 mM of cysteine maintained at a temperature of 39° C. under an atmosphere comprising 5% $CO_2$, 5% $O_2$ and 90% $N_2$ to promote maturation of the immature oocyte; followed by culture in a fresh culture medium without eCG and hCG to produce a mature recipient oocyte.

14. The method according to claim 5 wherein the treating step of the demecolcine to the activated fused oocyte to form the SCNT embryo results in producing a pseudo pronucleus from the nuclear donor cell introduced in the activated fused oocyte such that a polypoloidal (2n) DNA chromosomal state is maintained in the SCNT embryo.

15. The method according to claim 1 wherein the step of fusing comprises providing a cell fusion culture medium comprising a 0.28 M mannitol solution comprising 0.001 mM $CaCl_2$, and 0.05 mM $MgCl_2$.

16. The method according to claim 1 wherein the step of fusing comprises subjecting the enucleated oocyte containing the injected nuclear donor cell to a voltage applied twice at 1.4 kV/cm to 1.8 kV/cm for a duration of about 20 to 40 μsec.

17. The method according to claim 1 wherein the step of activating comprises transferring the fused embryo into a fresh activation medium comprising a 0.28 M mannitol solution comprising, 0.01 mM $CaCl_2$, and 0.05 mM $MgCl_2$ and subjecting the fused embryo to direct voltage applied twice at 1.2 kV/cm for a duration of 60 μsec.

18. The method according to claim 1 wherein the oocyte, prior to enucleation, is cultured in a maturation medium containing 5 IU of equine chorionic gonadotropin (eCG), 5 IU of human chorionic gonadotropin (hCG), 10 ng/ml of surface growth factor, 1 μg/ml of insulin and about 0.6 mM of cysteine maintained at a temperature of 39° C. under an atmosphere comprising 5% $CO_2$ to promote maturation of the immature oocyte;
    followed by culture in a fresh culture medium without eCG and hCG to produce a mature recipient oocyte.

* * * * *